United States Patent [19]

Kleinberg

[11] 4,225,579
[45] Sep. 30, 1980

[54] MEANS AND METHOD FOR IMPROVING DEFENSES AGAINST CARIES

[76] Inventor: Israel Kleinberg, 14 Three Pond Rd., Smithtown, N.Y. 11787

[21] Appl. No.: 15,635

[22] Filed: Feb. 27, 1979

Related U.S. Application Data

[60] Division of Ser. No. 868,933, Jan. 12, 1978, Pat. No. 4,154,813, and a continuation-in-part of Ser. No. 697,538, Jun. 18, 1976.

[51] Int. Cl.³ .................. A61K 9/68; A61K 7/22; A61K 37/00; C07C 103/52
[52] U.S. Cl. ................................ 424/48; 424/54; 424/177; 260/112.5 R
[58] Field of Search ................ 424/54, 48, 177; 260/112.5 R

[56] References Cited

U.S. PATENT DOCUMENTS

| 3,345,354 | 10/1967 | Kappeler, et al. | 260/112.5 R |
| 3,388,113 | 6/1968 | Guttmann et al. | 260/112.5 R |
| 3,856,770 | 12/1974 | Greven | 260/112.5 R |
| 3,932,608 | 1/1976 | Anderson et al. | 424/54 |

OTHER PUBLICATIONS

Blecher, et al., Liebigs Ann. Chem. 1973, 1263–1268.
Pettit, Synthetic Peptides, vol. I, 1970 pp. 82, 83, 88 and 89, 190 and 191.

*Primary Examiner*—Delbert R. Phillips

[57] ABSTRACT

Destruction of tooth tissues due to various microorganisms is slowed or prevented by introducing into the mouth arginine or an arginine precursor, especially peptides having from 2–4 amino acid units at least one of which is arginine.

9 Claims, No Drawings

MEANS AND METHOD FOR IMPROVING DEFENSES AGAINST CARIES

RELATED APPLICATION

This is a division of application Ser. No. 868,933, filed Jan. 12, 1973, U.S. Pat. No. 4,154,813 and a continuation in-part of applicant's Application Ser. No. 697,538 filed June 18, 1976.

BACKGROUND OF THE INVENTION

The present invention is based on two well accepted observations. Caries is more likely to occur when the pH of the mouth falls below a certain critical level depending on the resistance of the individual and on the duration for which the critical level is exceeded. The second observation is the recognition that saliva itself has a salutary effect on the aforementioned caries causing factors which include some means for raising oral pH.

THE PRESENT INVENTION

It has been clear for some time that when an abundance of carbohydrates, particularly sugar, is present in the mouth, conditions favoring the production of an acid pH in plaque are sure to be present. The plaque microflora form acid from exogenous or endogenous carbohydrate. The balancing of this acid production has been observed to be my means of producing alkaline substances which neutralize the cariogenic acids derived from the carbohydrates and return the pH of tooth surfaces to a level above that at which caries will occur.

The present invention relates to providing a means to enhance the natural defenses of the body against tooth caries when the latter are by cariogenic acids. It further is directed to replacing or supplementing the natural protective function of saliva when it is diminished by atrophy of the salivary glands or other impairments which diminish the secretion of saliva or the protective capability thereof.

It is an object of the present invention to provide a replacement or supplement to the caries protective portion of saliva.

It is a further object to diminish or eliminate caries in otherwise susceptible individuals by supplying suitable sources of pH adjusting compound or precursors thereof.

Another object of the present invention is the utilization of arginine precursors particularly peptides having 2-4 amino acid units, one or more of which is arginine as the pH adjusting means.

It has been observed that plaque, the closely adhering spongy organic material found on tooth surfaces accepts within its matrix molecules of certain size and shape. Peptides are among those compounds which can penetrate plaque. It has been shown that these compounds penetrate bacteria present in the mouth. It has been discovered that the material which most readily counteracts the acid produced when an abundance of carbohydrate, particularly sugar, is present is arginine. Surprisingly, it has been determined that peptide of 2-4 amino acid units, one or more of which is arginine, is effective in restoring mouth pH to a non-carious level.

It has been determined that generally, caries resulting from an acidic pH nearly invariably occurs when a pH of about 5 or 5.1 occurs for a sufficient time while with only rare exceptions will caries occur if the pH is maintained at 6.1 or higher.

The question of duration of exposure of enamel to a pH lower than about pH 5 varies with individuals but certain generalities have been determined. Two schemes of activity may be posited. In the first, the mouth is exposed to a limited amount of fermentable carbohydrate, usually sugar, after which the bacteria present in plaque convert the carbohydrate to acids, mainly acetic, lactic and propionic. In this case the pH drops as the above indicated acids are produced and a slow countering production of alkaline amines occurs as susceptible peptides or proteins give up amino acids which are decarboxylated by other oral bacteria. The two antagonistic reactions occur at rates such that the pH drop which is achieved between about 5 and 15 minutes will usually reach the pH level critical to the formation of caries unless the pH rise factor which has been found to be arginine and its precursors is present and is acted upon by oral bacteria so that the pH fall is reduced and the pH begins to return to the normal by the end of about 45 minutes to 1 hour depending upon the particular mouth.

A second situation is represented by an availability of greater amounts of fermentable carbohydrate available for a longer time. The mouth pH in this case goes below pH 5 which is conducive to the formation of caries after about 15 minutes and remains there while the excess of fermentable carbohydrate is available. This can be for a period of 2 or more hours. It is under these conditions that a more serious carious attack occurs but in the presence of the pH rise factor the duration is reduced.

Experiments were performed in vitro using supernatant saliva. The saliva was obtained from random donors whose salivary secretions were paraffin block stimulated. The saliva donations were pooled before and after sediment removal.

A naturally occuring effective peptide in saliva has the arrangement H-glycine-glycine-lysine-arginine-OH with amino and carboxyl termini. This compound was synthesized by conventional methods and has proven effective for the purposes of this invention and is a preferred pH rise factor. It being a compound which occurs naturally, it is a first choice, but the possibility of peptides having two or more arginine units might prove even more effective.

The arginine containing peptide rapidly enters plaque and also enters bacteria itself. The peptide is stored there protected from dilution providing a potential source of alkaline material to counter-act acid formation activated by the presence of dietary carbohydrate. This storage capability suggests inclusion of the peptide pH rise factor in common dental products such as tooth pastes, tooth powders, mouthwashes, chewing gum and the like.

It has further been found that the oligomeric peptide pH rise factor is effective even when provided to the mouth simultaneously with carbohydrate substances which are operated upon by plaque bacteria to produce acids. The addition of the pH rise factor to carbohydrate containing substances such as sugared cereals, candy or chewing gum is an effective means for supplementing the natural defenses of the body against caries.

The arginine containing peptides are particularly suited as food additives in that many occur in nature, particularly the preferred one of the present invention.

They are generally heat stable, tasteless, odorless and soluble in amounts beyond their effective level. They are esthetically acceptable as used.

The pH differences in the mouths of caries prone and caries free subjects can be minimized by adding pH rise factor supplement to the former. This is effective in proportion to the amounts of an arginine containing peptide provided. A significant effect is produced with as little as 0.05 mM while as much as 3 mM and more continued to show improvement.

Particularly interesting cooperation between the pH rise factor and fluoride ions has been observed. Fluoride ions in minor amounts such as about 5 ppm reduces tooth solubility generally. It further inhibits the pH fall when the pH drops below about 5. The pH fall in the case of high sugar availability to 4.8 is held to 5.1 when 5 ppm of fluoride is present. This is about as high as fluoride ions alone can return the pH. When the pH rise factor of the present invention is also present, fluoride still inhibits the pH fall but the pH recovers earlier to safe levels of pH than when no factor is present.

The following are given by way of exemplification and not by way of limitation.

Four sets of three 10×75 mm test tubes were provided with 0.2 ml of 8.4 mM (millimolar) of aqueous glucose solution. Set I was provided with 0.2 ml of pooled supernatant saliva. Set II was provided with 0.2 ml of 9.9 mM of the peptide glycine-glycine-arginine. Set III was provided with 0.2 ml of 9.9 mM arginine. Set IV was provided with 0.2 ml of distilled water. Sequentially 0.2 ml of a 50:50 aqueous suspension of oral bacteria was added to each test tube. The concentration of the peptide in the combined composition was 3.3 mM. The prepared test tubes were kept at 37° C. in a water bath. pH readings were taken at 0 time when the bacteria was added and at 15, 30, 45, 60, 90, 120, 180 and 240 minutes. The pH values are as follows:

| TIME (minutes) | 0 | 15 | 39 | 45 | 60 | 90 | 120 | 180 | 240 |
|---|---|---|---|---|---|---|---|---|---|
| Set I | 7.4 | 6.2 | 5.9 | 6.1 | 6.3 | 6.4 | 6.5 | 6.6 | 6.6 |
| Set II | 7.4 | 6.8 | 6.6 | 6.4 | 6.6 | 6.6 | 6.7 | 7.2 | 7.6 |
| Set III | 7.3 | 5.8 | 5.4 | 5.2 | 4.9 | 5.0 | 5.0 | 5.3 | 5.8 |
| Set IV | 7.3 | 5.8 | 5.2 | 4.9 | 4.7 | 4.6 | 4.3 | 4.5 | 4.5 |

It is clear that supernatant saliva and an arginine providing supplement slows the pH fall in a carbohydrate rich environment. It is also evident that an arginine providing peptide is preferred to arginine alone. In similar experiments, an arginine providing peptide supplement acts to moderate the pH drop more than either saliva alone or arginine alone and restores the pH to its initial level or better.

The identification of the arginine providing peptide pH rise factor suggests other areas wherein arginine containing peptides could be utilized. These compounds could be used in the regulation of many processes involving microorganisms such as bacterial fermentations, wine making, antibiotic production, citric acid formation and others.

Extensive testing of individual peptides of 2-4 amino acid units as could reasonably be obtained or synthesized was done. The tests were carried out under the same conditions as Sets I-IV. The salivary sediment was present in an amount of 16.7% (v/v), glucose 2.8 mM and the peptide 3.3 mM in the final composition. Duplicate runs without peptide were run parallel to the others as a double check. The pH starts at slightly above 7 and falls rapidly to between 4.5-5. An effective pH rise factor begins to reverse the fall within the first hour. Measurement continues through the fourth hour. The results were as follows:

| | |
|---|---|
| Arg-Leu | pH drop to 5.5, rising to about 7-8 |
| Lys-Leu | pH drop to 5.2 rising to about 5.5 |
| Pro-Pro | no significant pH rise |
| Pro-Pro-Pro | no significant pH rise |
| Pro-Ala | no significant pH rise |
| Meth-Pro | no significant pH rise |
| Arg-Ser | pH drop to about 5.5, rising to about 7. |
| Lys-Ser | pH drop to about 5.3, rising to about 5.6 |
| His-Meth | pH drop to about 5.4, rising to about 5.5 |
| Asp-Arg | pH drop to about 5.4, rising to about 6.8 |
| Phe-Arg | pH drop to about 5, rising to 6.8-7.8 |
| Gly-Arg | pH drop to about 5.2, rising to 7.5 |
| Arg-Gly | pH drop to about 5.5, rising to 7-7.9 |
| Arg-Lys | pH drop to about 6-6.7, rising to 7.2-8 |
| Gly-Gly-Pro | no significant pH rise |
| Gly-Gly-Gly | no significant pH rise |
| Gly-Gly-Arg | pH drop to 5.5, rising to 7.5 |
| Gly-Gly-Lys-Arg | pH drop to 6.4, rising to 8.4 |

It is clear from the representative results that peptides of 2-4 amino acid units one or more of which is arginine constitute providers of a pH rise factor. This is so whether the arginine moiety as linked to the other amino acids of the peptide by the carboxyl or amino group.

The invention has been described with respect to certain preferred embodiments but it will be understood that variations and modifications may be made therein without departing from the spirit of this invention and the scope of the appended claims.

What is claimed is:

1. A composition selected from the group consisting of a dental care product, a food product and a chewing gum which comprises a source of pH adjusting compound or precursor thereof having 2-4 amino acid units of which at least one unit is arginine, in an amount effective to combat caries by controlling oral pH.

2. The composition of claim 1 wherein said amount is sufficient to release from about 0.05 to about 3 mM of said pH adjusting compound or precursor in the oral cavity.

3. The composition of claim 1 wherein the major portion thereof is a dental care product.

4. The composition of claim 1 wherein the major portion thereof is a food product.

5. The composition of claim 1 wherein the major portion thereof is a chewing gum.

6. The composition of claim 3 which contains an effective amount of fluoride ions.

7. The composition of claim 1 wherein said amino acid units have a sequence selected from the group consisting of: Arg-Leu; Arg-Ser; Asp-Arg; Phe-Arg; Arg-Gly; Arg-Lys; Gly-Gly-Arg; and Gly-Gly-Lys-Arg.

8. The composition according to claim 1, wherein said amino acid units comprise a dipeptide of arginine and lysine, wherein said arginine moiety is linked to said lysine moiety by its carboxyl or amino group.

9. The composition of claim 1 wherein said amount is adequate to restore oral pH to a non-carious level.

* * * * *